United States Patent [19]

Carter

[11] Patent Number: 4,724,869
[45] Date of Patent: Feb. 16, 1988

[54] FLOW SELECTOR DEVICE
[75] Inventor: William Carter, Indianapolis, Ind.
[73] Assignee: Ray V. Bussell, Greenfield, Ind.
[21] Appl. No.: 29,089
[22] Filed: Mar. 23, 1987
[51] Int. Cl.[4] .......................... F16K 3/32; F16K 51/00
[52] U.S. Cl. ........................................ 138/45; 138/46; 251/205; 251/206
[58] Field of Search ..................... 138/37, 39, 40, 42, 138/43, 44, 45, 46; 251/206, 208, 205, 207

[56] References Cited
U.S. PATENT DOCUMENTS 3,741,229 6/1973 Gruver ........................... 251/206 X
4,241,896 12/1980 Voege ................................ 251/206
4,366,947 1/1983 Voege ................................. 138/45
4,655,246 4/1987 Phlipot et al. ................. 251/206 X Primary Examiner—James E. Bryant, III
Attorney, Agent, or Firm—Robert A. Spray

[57] ABSTRACT

A flow selector device whose fluid flow is regulated by the rotational setting of a rotor body in a housing; and a split retainer form of an abutment, releasably held between opposed abutments of the rotor body and the housing body, serves to restrain the rotor body against movement axially of the housing as otherwise would be urged by the axial force result of the actuation of a spring pressed rotor-indexing detent feature and of a sealing feature, both of which are carried by the housing and have an effect of pushing the rotor body axially of the housing due to their compressive nature.

12 Claims, 2 Drawing Figures

FLOW SELECTOR DEVICE

FIELD OF THE INVENTION

The present invention relates to a flow selector device, and the invention provides a retainer for the rotatable rotor body of the selector device which is very economical, yet is quite operable and dependable; and although it will provide long-life service, it is easily removable for whatever servicing may be desired to the interior components of the device, and easy then to re-install in the re-assembly of the rotor in the device's housing.

Such flow selectors may find wide service, for a controlled flow of gas or liquid; but since they have a particularly desirable use in gaseous oxygen systems for vital oxygen supply to a patient, and since in particularly such use their interior components need to be closely monitored for flow-rate, it is particularly advantageous in such applications to make dis-assembly and re-assembly easy and convenient to an authorized servicer but to conversely make the tampering and dis-assembly difficult for a user who may attempt to dis-assemble the device for purposes which would violate the physician's instructions as to its settings, output, etc.

Even after the device's control knob would be removed, a desire for a device for oxygen-supply use is that its further dis-assembly would not be obvious, in any unauthorized tampering procedure; and a corresponding achievement of the concepts of this invention is that the rotor-retainer means, even after the control knob is removed, gives only minimal clue as to its function and to its consequent dis-assembly role.

PRIOR ART

As Emphasizing Inventive Nature of this Invention

Retainers which resist axial movement of a rotational component, such as a shaft, are of course themselves known; but the inventor knows of none having the features of operativty, assembly-role, and dis-assembly role particularly as herein set forth; and the disguising nature and effect of the retainer concepts here, together with its other aspects, as herein set forth, provide the flow selector device with its advantageous operativity and inventive nature more fully described below.

Thus, although it is even emphasized that the retainer means here is similar to other retainers, in that it provides an abutment device fitting between opposed abutments on a rotor and a fixed part (here the housing), nevertheless the differences between this retainer means and others such as C-clips, U-clips, ring members fastened onto a shaft, etc., show that conceptually here the differences from such prior art are of inventive nature, as will become more apparent as the detailed features are pointed out and considered more specifically as to nature and effect.

BRIEF SUMMARY OF THE INVENTIVE CONCEPTS

The inventive concepts are provided for a flow selector device which has as basic components a rotor body rotatably carried in a housing shell, with the rotor body carrying a plurality of orifices for providing optionally-selected rates of flow, depending on the rotational setting of the rotor.

An indexing detent means forces only specific settings of the rotor, presenting each selected orifice to be a flow-registry with the housing's outlet; and the outlet has a seal which pushes against the rotor to seal that registry of flow-control orifice and outlet.

With such a device, the inventive concepts provide a retainer feature for the rotor, and block the rotor against the axial movement as urged by both the force of the indexing detent means and the force of the outlet seal against the rotor.

Oppositely-facing abutments are provided on both the rotor shaft and the housing, the housing abutment being in the form of a seat or recess; and between those abutments, and from opposite lateral sides, there are pushed a pair of abutment pieces, each in the form of a segment or sector of a ring of a shape generally concentric with the axis of the rotor.

The retainer abutment pieces, when so installed, provide hardly any indication of their role in retaining the rotor, and, as seated in the seat-type abutment of the housing, they are firmly held against withdrawal laterally; and thus the retainer pieces not only maintain the assembly against unauthorized dis-assembly, but are easily removed by an authorized person for servicing the interior components of the device.

BRIEF DESCRIPTION OF THE DRAWINGS

The above description is of somewhat introductory and generalized form. More particular details, concepts, and features are set forth in the following and more detailed description of an illustrative embodiment of a flow selector device of the invention, taken in conjunction with the accompanying drawings, which are of somewhat schematic and diagrammatic nature for showing of the inventive concepts, as well as illustrating the ease and convenience of assembly and dis-assembly of device's rotor from its housing, as provided by its novel rotor-retainer feature.

In the drawings.

DETAILED DESCRIPTION OF PREFERRED EMBODIMENT

Figures 1, 2:
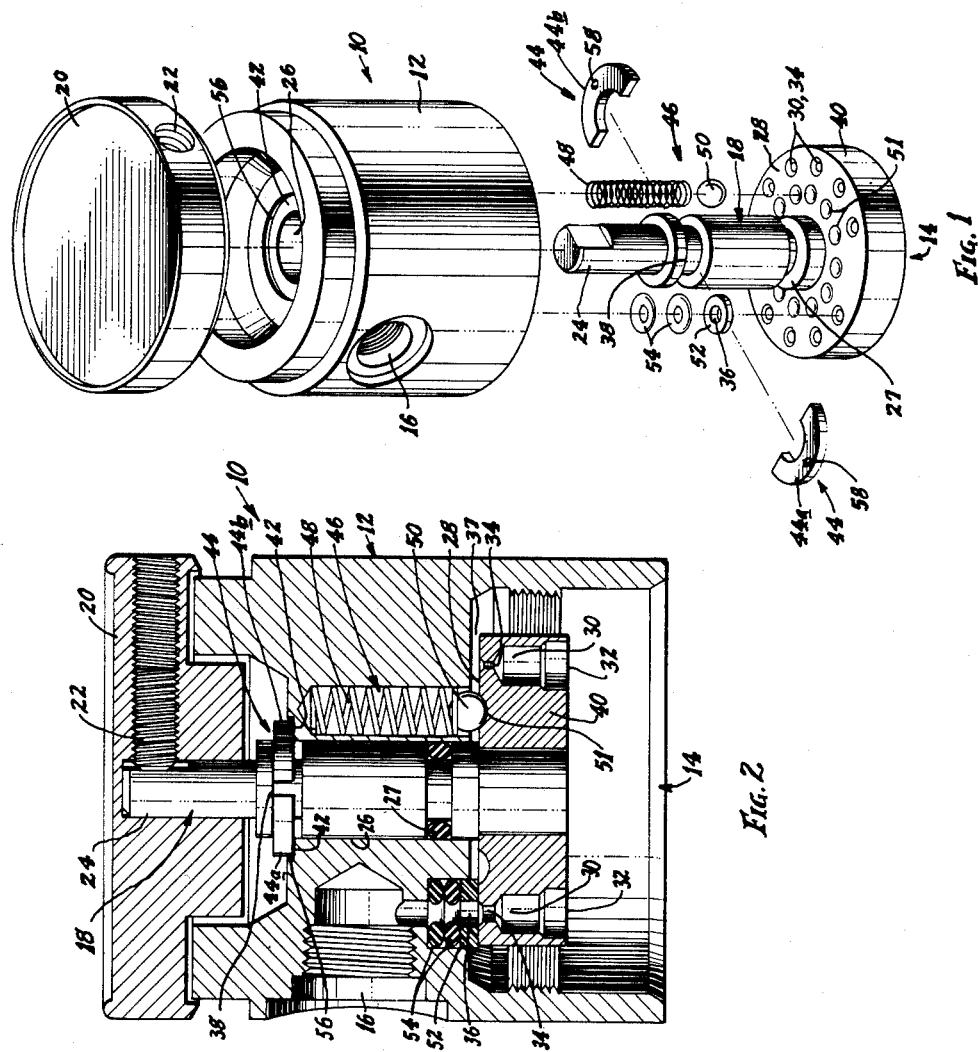
FIG. 1, of isometric nature or showing of the components, is a so-called "exploded view" of a flow selector device of an illustrative embodiment, its "exploded" components being shown as inter-related by broken lines, along which the components would move into the assembly of FIG. 2, as is the nature of an "exploded view"
FIG. 2 is an assembly view, generally in axial cross-section, of the device shown in FIG. 1.

As shown in the drawings, the invention provides an advantageous flow selector device 10 particularly useful and desirable for supplying a desired rate of flow of a gaseous fluid, and particularly that of gaseous oxygen in an oxygen supply system.

The external housing or shell for the device 10 as shown is a housing body means 12; and as shown in the drawings the gas flow is upwardly and leftwardly, i.e., upwardly through the housing 12's inlet means 14 and leftwardly out its outlet means 16. Both the inlet 14 and outlet 16 are threaded for connection of associated fittings (not shown) which may be made fluid-tight as by O-rings or the like (not shown).

The rate of flow is controlled by a rotor body means 18, it being manipulatable by a control knob 20 connected by a set screw 22 to a shaft 24 of the rotor body means 18; and the rotor body means 18 is supported by the housing body means 12 in a bore 26 thereof so as to be rotationally movable with respect to the housing body 12. An O-ring 27 is shown as blocking flow of fluid along the bore 26.

With further reference to the selector control means for rotating the rotor 18 relative to the housing 12 to achieve optionally-desired flow from the housing 12's outlet means 16, the rotor body 18 is shown provided with a transversely extending face 28; and a plurality of passageway 30 extend axially through the rotor body 18, the inlet 32 of all of such passageways 30 being open to the housing body inlet 14, and the outlet 34 of each passageway 30 being open to the rotor face 28.

As diagrammatically indicated by the difference in size of the passageways 34 in FIG. 2, the difference in fluid flow, to achieve the desired flow rate out the outlet 16, is diagrammatically shown merely by those size differences in FIG. 2, for that is not a part of the present invention.

The outlet 34 of only one of such passageways 30 is registrable with the upstream end 36 of the housing body outlet means 16 in any particular rotational setting of the rotor body 18 with respect to the housing 12, thus achieving the option of flow-rate. That is, the upstream end, or inlet, 36 of the housing outlet 16 is restricted so as to receive fluid from only one of the passageways 30, thus to deliver through outlet 16 only the fluid rate, as permitted by a single chosen one of the passageways 30, by the inter-related features of support of the rotor body means 18, and the rotor body 18 itself, and the rotor face 28 being such that the rotor face 28 is in axial alignment with the upstream inlet opening 36 of the housing 12's outlet means 16 regardless of the rotational setting of the rotor body means 18, even though only a particular one passageway outlet 34 can be in registry with the housing outlet 16's inlet 36.

(Downstream (up in FIG. 2) of the rotor face 28, fluid from other passageway outlets 34 may enter housing chamber 37, but flow therefrom is sealed by the seal 27.)

In the device 10 the housing body 12 carries certain compression means, as specified below, which urge the rotor body 18 axially of the housing body 12 toward the housing inlet 14; and it is such compression means which are resisted by special retainer feature of the present concepts.

Such retainer means for the rotor body 18, which resist the effect of the compression means, are shown as including an abutment means 38 on the rotor 18 (particularly as shown as a downwardly-facing shoulder on the rotor shaft 24) which faces the portion 40 of the rotor body 18 having the passageways 30, an abutment means 42 carried by the housing body means 12 (particularly as shown on the portion thereof shown at the top in the drawings), and an abutment means 44 which is operatively abuttingly engageable between the abutment means 38 of the rotor body 18 and the abutment means 42 of the housing body 12; and by the abutment means 44 providing abutting engagement for more than 180° of the circumferential extent of the rotor body 18 and of the housing body 12, that abutment means 44 is operative to restrain the rotor body 18 against the movement as urged by whatever is the compression means.

More particularly as shown, the abutment means 44 is provided by at least two discrete pieces, as segments 44a and 44b, of a ring shape concentric about the axis of the rotor body 18; and each of the two pieces 44a and 44b is slightly less than 180° in arcuate extent.

Now are specified compression means which the novel retainer means (44, etc.) resist, which otherwise would push the rotor 18 axially (downwardly, in the drawings).

One of such compression means tending to push the rotor 18 axially is an indexing detent means 46 which is operative between the housing body 12 and the rotor body 18. The detent means 46 is shown as a spring 48 and a detent ball 50, there being an annular series of recesses 51 cut in rotor face 28 for controlling the rotational position of the rotor 18 to assure it to be in only a position of registry of only a single passageway 30 or an "off" position; but its spring-urge nature causes it to have an effect of urging the rotor body 18 axially of the housing body 12, that axially-urging effect being a compression means effect which is restrained by the abutment means 44, etc., as mentioned above.

There is another compression means whose axial-moving effect on the rotor 18 is restrained by the abutment means 44, etc., and that is a seal means 52 at the upstream end 36 of the housing 12's outlet means 16 and which is spring-pressed sealingly toward the face 28 of the rotor body means 18. This spring-pressing of the seal means 52 against the rotor body face 28 is restrained, as is the force of the detent means 46, by the abutment means 44, etc.

In the form shown, the sealing contact body of the seal 52 is provided by a ring-shaped body known as a KEL-F seal, and its sealing force or pressure is caused by an axially-stacked pair of O-ring means 54 carried by the housing body 12 adjacent the upstream end 36 of the housing's outlet means 16; and it is the force of those O-rings 54 which is restrained by the abutment means 44, etc.

The rotor movement-blocking effect of the abutment pieces 44a and 44b, in their sealing upon the abutment ledge or flange 42, is more assured by them fitting radially inwardly of a circular wall means 56 which blocks their radially outward movement off the ledge 42. The wall 56 is shown as very short in its axial extent, thus making easy to install the retainer pieces 44a and 44b, and minimizing the thickness needed for those pieces 44a and 44b which bear against the shaft shoulder 38. The wall 56 and seat 42 provide a recess for the pieces 44.

The retainer pieces 44a and 44b are releasably carried in that abutting position between the rotor abutment 38 and the housing abutment 42; and they are shown as provided with a lug means, here shown merely as small holes 58, for facilitating release of the abuttingly engageable abutment pieces 44a and 44b from their abutting position.

Such concepts minimize the likelihood that many users could successfully tamper with the device to achieve its dis-assembly, for the pieces 44a and 44b are snugly carried with hardly a hint or clue as to their role in assembly or dis-assembly; and the difficulty of unauthorized dis-assembly is further magnified by the requirement that the rotor body 18 need be raised relative to the housing 12 for withdrawal of the pieces 44a and 44b past the wall 56, even though the compressive forces of the detent spring 48 and the O-rings 54 are pushing the rotor body 18 downwardly, yet the spring 48 and O-rings 54 are hidden from view.

CONCLUSION

It is thus seen that a flow selector device constructed and assembled according to the inventive concepts herein set forth, particularly as to the retainer means for the rotor body, provides a desired and advantageous device, yielding the advantages of a desired and advantageous flow selector useful for many uses of fluid flow.

Accordingly, it will thus be seen from the foregoing description of the invention according to this illustrative embodiment, considered with the accompanying drawings, that the present invention provides a combination new and useful concepts of a novel and advantageous flow selector device, and particularly a novel and advantageous retainer of the rotor body as restraining against compressive forces urging the rotor body to move axially of the device housing, having and yielding desired advantages and characteristics in construction and use, and accomplishing the intended objects, including those hereinbefore pointed out and others which are inherent in the invention.

Modifications and variations may be effected without departing from the scope of the novel concepts of the invention; accordingly, the invention is not limited to the specific embodiment, or form or arrangement of parts herein described or shown.

I claim:

1. A flow selector device, comprising, in combination,
   a housing body means provided with an inlet means and an outlet means,
   a rotor body means supported by the housing body means to be rotationally movable with respect thereto,
   selector control means for rotating the rotor body means relative to the housing body means to achieve optionally-desired flow from the outlet means of the housing body means;
   the rotor body means being provided with a transversely extending face and a plurality of passageways extending axially through the rotor body means, the inlet of all of such passageways being open to the housing body inlet means but the outlet of only one of such passageways being registrable with the upstream end of the housing body outlet means in any particular rotational setting of the rotor body means with respect to the housing body means, although the outlet of all said passageways opening to the said rotor face,
   the support of the rotor body means, and the rotor body means, and its said face, being such that said face is in axial alignment with the upstream opening of the outlet means of the housing body means, regardless of the rotational setting of the rotor body means, even though only a particular one passageway outlet can be in registry therewith,
   the housing body means carrying compression means which urge the rotor body means axially of the housing body means toward the inlet means thereof,
   and a retainer means for the rotor body means, the retainer means comprising:
   (a) the provision of the rotor body means to have an abutment means facing the portion of the rotor body means having the said passageways, and
   an abutment means carried by the housing body means, and
   the provision of an abutment means operatively abuttingly engageable between the said abutment means of the rotor body means and the said abutment means of the housing body means,
   the said operatively abuttingly engageable abutment means providing the said abutting engagement for more than 180° of the circumferential extent of the rotor body means and of the housing body means, and operative to restrain the rotor body means against the movement as urged by the compression means.

2. A device as set forth in claim 1, in which the said operatively abuttingly engageable abutment means is provided by at least two discrete pieces, providing the operative abutting contact of more than the 180° as specified.

3. A device as set forth in claim 2, in which the pieces of the operatively abuttingly engageable abutment means are provided to be segments of a ring shape concentric about the axis of the rotor body means.

4. A device as set forth in claim 3, in which there are two pieces, each of which is slightly less than 180° in arcuate extent.

5. A device as set forth in claim 1, in which there is provided a detent means, operative between the housing body means and the rotor body means, the detent effect thereof also having an effect in urging the rotor body means axially of the housing body means, and said axially urging effect is restrained by the operatively abuttingly engageable abutment means.

6. A device as set forth in claim 1, in which the rotor body means is provided with seal means at the upstream end of outlet means of the housing body means, and is spring-pressed toward the said face of the rotor body means, the spring-pressing of the seal means against the rotor body means face being restrained by the operatively abuttingly engageable abutment means.

7. A device as set forth in claim 5, in which the rotor body means is provided with seal means at the upstream end of outlet means of the housing body means, and is spring-pressed toward the said face of the rotor body means, the spring-pressing of the seal means against the rotor body means face being restrained by the operatively abuttingly engageable abutment means.

8. A device as set forth in claim 1, in which the rotor body means includes a shaft means, and the said rotor body means' abutment means, which faces the portion of the rotor body means having the said passageways, is provided as a shoulder provided on said shaft.

9. A device as set forth in claim 1, in which there are provided one or more O-ring means carried by the housing body means adjacent the upstream end of the housing body means outlet means, and provide means which spring-press the seal means toward said face of the rotor body means, the force of said O-ring means being a force upon the rotor body means whose movement in response thereto is restrained by the operatively abuttingly engageable abutment means.

10. A device as set forth in claim 1, in which the housing body means is provided with a wall means blocking radially outward movement of the operatively abuttingly engageable abutment means.

11. A device as set forth in claim 1, in which the operatively abuttingly engageable abutment means is releasably carried in its abutting position as specified above.

12. A device as set forth in claim 11, in which the operatively abuttingly engageable abutment means is provided with a lug means for facilitating release of the operatively abuttingly engageable abutment means from its said abutting position.

* * * * *

UNITED STATES PATENT AND TRADEMARK OFFICE
CERTIFICATE OF CORRECTION

PATENT NO.   :   4,724,869
DATED        :   February 16, 1988
INVENTOR(S)  :   William Carter It is certified that error appears in the above-identified patent and that said Letters Patent is hereby corrected as shown below:

<u>Col. 3, line 8</u>;   Change "passageway" to "passageways"

Signed and Sealed this

Second Day of August, 1988

Attest:

DONALD J. QUIGG

*Attesting Officer*          *Commissioner of Patents and Trademarks*